United States Patent [19]

de Nanteuil et al.

[11] Patent Number: 5,567,804
[45] Date of Patent: Oct. 22, 1996

[54] PEPTIDES DERIVED FROM TRIFLUOROMETHYLKETONES

[75] Inventors: Guillaume de Nanteuil, Suresnes; Bernard Portevin, Elancourt; Emmanuel Canet, Paris, all of France

[73] Assignee: Adir et Compagnie, Courbevoie, France

[21] Appl. No.: 437,433

[22] Filed: May 5, 1995

[30]  Foreign Application Priority Data

May 5, 1994 [FR] France .................................. 94 05494

[51] Int. Cl.$^6$ .................................................. A61K 38/06
[52] U.S. Cl. .......................... 530/331; 530/345; 530/350; 514/18
[58] Field of Search ............................. 514/18; 530/331, 530/350, 323, 345

[56]  References Cited

U.S. PATENT DOCUMENTS 5,296,591  3/1994  Hemmi et al. ........................... 530/331
5,430,025  7/1995  Hemmi et al. ........................... 530/331

FOREIGN PATENT DOCUMENTS 2101350  1/1994  Canada .

*Primary Examiner*—Elizabeth C. Weimar
*Assistant Examiner*—Anish Gupta
*Attorney, Agent, or Firm*—The Firm of Gordon W. Hueschen

[57]  ABSTRACT

Compounds of formula (I):

[structure of formula (I)]

in which:

$R_1$ represents alkyl or ($C_3$–$C_7$) cycloalkyl $R_2$ represents alkyl, or ($C_3$–$C_7$) cycloalkyl, $R_3$ represents hydrogen or alkyl, $R_4$ represents halogen or alkyl or alkoxy, $R_5$ represents alkyl, X and Y, which are different, represent CO or $SO_2$, n represents 1, 2 or 3, p represents 0 or 1, Z represents sulfur or oxygen, A represents any one of the following groups:

$$-\underset{\underset{A_1}{\diagdown\diagup}}{N}-CH-$$

in which:

$A_1$ represents, with the nitrogen and carbon atoms to which it is attached, a mono- or bicyclic heterocycle,

• or, $$-\underset{R_6}{N}-\underset{R_7}{CH}-,$$

in which:

$R_6$ represents hydrogen, alkyl or cycloalkyl or 2-indanyl, $R_7$ represents hydrogen or alkyl, which compounds of formula (I) comprise thereof corresponding hydrates of the ketone function $COCF_3$, the enantiomers, diastereoisomers and epimers thereof and the addition salts thereof with a pharmaceutically acceptable base and medical products containing the same are useful as HLE inhibitor.

9 Claims, No Drawings

PEPTIDES DERIVED FROM TRIFLUOROMETHYLKETONES

BACKGROUND OF THE INVENTION

The present invention relates to new peptides derived from trifluoromethylketones.

FIELD OF THE INVENTION

These new peptide derivatives possess inhibitory properties towards human leucocyte elastase. In addition, these compounds possess antioxidant properties.

Elastin is an elastic fibrous protein of the conjunctive tissue of vertebrates. It is present in the vascular walls, the skin, the lungs, cartilage, ligaments and other tissues. Elastases are enzymes capable of solubilizing fibrous elastin. Human leucocyte elastase is a serine protease which is found in active form in the azurophilic granules of polymorphonuclear neutrophils. This is a 25- to 30-kDa glycoprotein formed of 218 amino acids. Human leucocyte elastase (HLE) solubilizes fibrous elastin, but also cleaves other proteins of the extracellular matrix (collagens, fibronectin, proteoglycans, etc.), and hydrolyzes and inactivates a certain number of plasma proteins (coagulation factor, immunoglobulin, complement, etc.). The elastolytic activity is controlled and regulated by natural inhibitors (alpha 1-antitrypsin, alpha 2-macroglobulin, the bronchial inhibitor) which are sensitive to oxidizing agents.

Reversible and irreversible human leucocyte elastase inhibitors have been described in the literature for the treatment of physiopathological conditions in which its role has been mentioned (D. A. TRAINOR, TIPS, 8, 303–307, 1987).

These pathological states may be pulmonary emphysema, rheumatoid arthritis, degenerative diseases of the conjunctive tissue such as atherosclerosis (J. G. BIETH, "Elastases: Catalytic and Biological Properties" in "Regulation of matrix accumulation" - R. P. MECHAM - Academic Press, N.Y., 217–320, 1986), the syndrome of acute respiratory distress in adults (P. M. SUTER et al., Am. Rev. Respir. Dis., 145, 1016–1022, 1992), cystic fibrosis (K. C. MEYER et al., Am. Rev. Respir. Dis., 144, 580–585, 1991), chronic bronchitis (J. A. NADEL, Respiration, 58 (suppl. 1, 3–5), 1991), glomerulonephritis (E. SANDERS et al., Renal. physiol., 3, 355–359, 1980), psoriasis (J. SCHALKWIJK et at., Br. J. Dermatology, 122, 631–644, 1990), and tissue lesions arising during ischemia-reperfusion processes (F. A. NICOLINI et al., Am. HEART J., 122–1245, 1991 and C. R. B. WELBOURN et al., Am. J. Physiol. 260, 1852–1856, 1991). It may also play a role in normal or pathological tumor invasion cell migration phenomena (J. G. BIETH cited above).

DESCRIPTION OF THE PRIOR ART

Recently, peptides derived from trifluoromethyl ketones have been described as HLE inhibitors. This is the case, more particularly, of the compounds described in patents EP 189,305 and EP 369,391.

DETAILED DESCRIPTION OF THE INVENTION

The present invention relates more specifically to the compounds of formula (I):

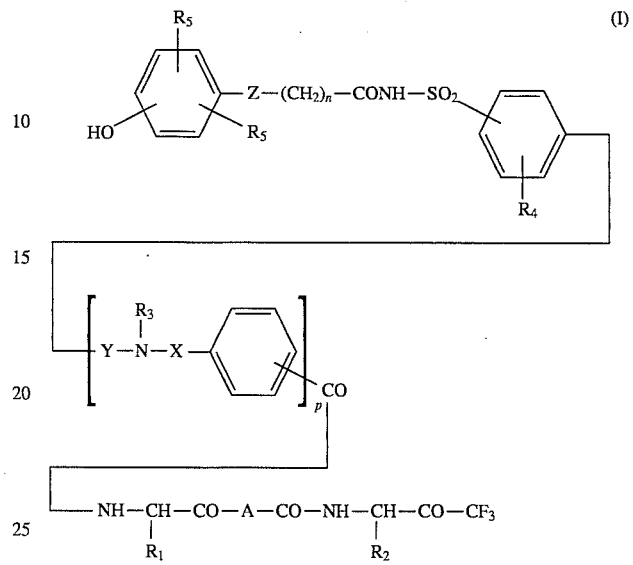

in which:

$R_1$ represents a linear or branched ($C_1$–$C_6$) alkyl group or a ($C_3$–$C_7$) cycloalkyl group, $R_2$ represents a linear or branched ($C_1$–$C_6$) alkyl group or a ($C_3$–$C_7$) cycloalkyl group, $R_3$ represents a hydrogen atom or a linear or branched ($C_1$–$C_6$) alkyl group, $R_4$ represents a halogen atom or a linear or branched ($C_1$–$C_6$) alkyl group or a linear or branched ($C_1$–$C_6$) alkoxy group, $R_5$ represents a linear or branched ($C_1$–$C_6$) alkyl group, X and Y, which are different, represent CO or $SO_2$, n represents 1, 2 or 3, p represents 0 or 1, Z represents a sulfur or oxygen atom, A represents any one of the following groups:

*

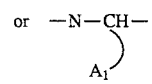

in which:

$A_1$ represents, with the nitrogen and carbon atoms to which it is attached, a 2-azabicyclo[2.2.2]octane, 2-azabicyclo[2.2.1]heptane, perhydroindole, perhydroisoindole, indoline, isoindoline, perhydroquinoline, perhydroisoquinoline, 1,2,3,4-tetrahydroisoquinoline, 1,2,3,4-tetrahydroquinoline, icyclopenta[b]pyrrolidine, 1,3-thiazolidine or pyrrolidine ring system,

• or,

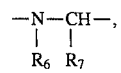

in which:

$R_6$ represents a hydrogen atom, a linear or branched ($C_1$–$C_6$) alkyl group, a ($C_3$–$C_6$) cycloalkyl group or a 2-indanyl group, R7 represents a hydrogen atom or a linear or branched ($C_1$–$C_6$) alkyl group, which compounds of formula (I) comprise the corresponding hydrates of the ketone function $COCF_3$,
the enantiomers, diastereoisomers and epimers thereof and the addition salts thereof with a pharmaceutically acceptable base.

Among the pharmaceutically acceptable bases which may be mentioned, without any limitation, are sodium hydroxide, potassium hydroxide, tert-butylamine, diethylamine, ethylenediamine, etc.

The invention also covers the process for the preparation of the compounds of formula (I), wherein an alcohol of formula (II) is used as starting material, the isomers of which alcohol have optionally been separated by a standard separation technique:

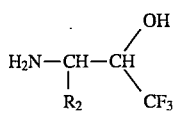  (II)

in which $R_2$ has the same meaning as in the formula (I), which alcohol is reacted:
a either with a protected amino acid of formula (IID), the isomers of which have optionally been separated according to a standard separation technique, by a standard peptide coupling technique such as that described by W. KONIG and R. GEIGER (Ber., 103, 788, 1970):

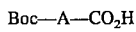  (III)

in which A has the same meaning as in formula (I) and Boc represents a tert-butoxycarbonyl group, to give the compound of formula (IV):

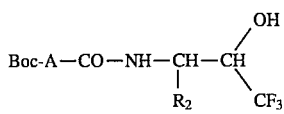  (IV)

in which A, $R_2$ and Boc have the same meaning as above, which compound of formula (IV):
* either is deprotected via acid hydrolysis to give the compound of formula (V):

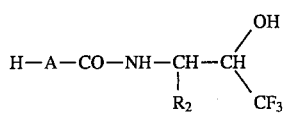  (V)

in which A and $R_2$ have the same meaning as above, with which compound a protected amino acid of formula (VI) is reacted, the isomers of which have optionally been separated according to a standard separation technique, in the presence of a standard coupling agent of peptide synthesis:

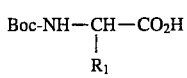  (VI)

in which Boc represents a butoxycarbonyl radical and $R_1$ has the same meaning as in formula (I), to give the compound of formula (VII):

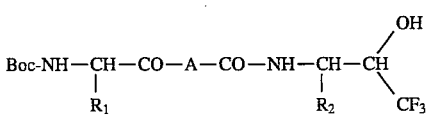  (VII)

in which Boc, $R_1$, A and $R_2$ have the same meaning as above, which compound undergoes an oxidation to give the compound of formula (VIII), the isomers of which are optionally separated according to a standard separation technique,

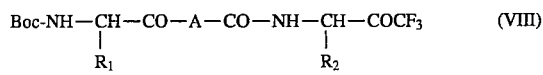  (VIII)

in which Boc, $R_1$, A and $R_2$ have the same meaning as above,
* or undergoes an oxidation to give the compound of formula (X):

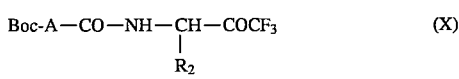  (X)

in which Boc, A and $R_2$ have the same meaning as above, which compound is deprotected in acidic medium to give the compound of formula (XI):

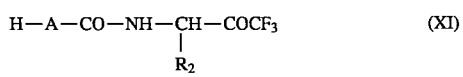  (XI)

in which A and $R_2$ have the same meaning as above, which compound is reacted with a protected amino acid of formula (VI) as defined above,
to give the compound of formula (VIII) defined above,
b or with a protected dipeptide of formula (XII), obtained by standard coupling of two amino acids in racemic form or in the form of pure enantiomers,

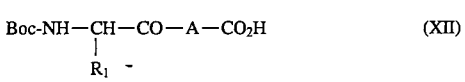  (XII)

in which Boc, $R_1$ and A have the same meaning as above, to give the compound of formula (VII) defined above, which undergoes an oxidation and gives the compound of formula (VIII) defined above,
which compound of formula (VIII) is deprotected in acidic medium, to give the compound of formula (IX), the isomers of which are optionally separated according to a standard separation technique,

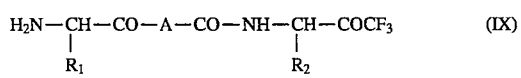  (IX)

in which $R_1$, A and $R_2$ have the same meaning as above, which compound is reacted with an acid of formula (XIII), according to a standard peptide coupling technique, (XIII)

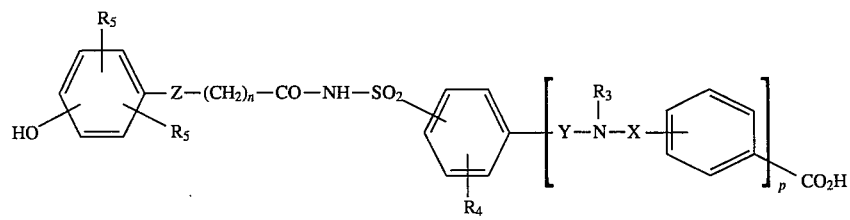

in which $R_5$, Z, n, p, $R_4$, $R_3$, X and Y have the same meaning as in formula (I), to give the compound of formula (I), which compound of formula (I) is purified according to a standard purification technique, the isomers of which are separated, if so desired, according to a standard separation technique, and which is then, if required, converted into an addition salt with a pharmaceutically acceptable base.

The compounds of formula (I) possess very advantageous pharmacological properties, in particular human leucocyte elastase inhibitory properties. In this respect, they may profitably be used in a certain number of therapeutic indications such as pulmonary emphysema, chronic bronchitis, acute respiratory distress syndrome in adults, cystic fibrosis, rheumatoid arthritis, glomerulonephritis, inflammations, ischemia reperfusion syndromes, phenomena of invasion and of diffusion of malignant cells, degenerative diseases of the conjunctive tissue, and ageing of the skin.

The inhibitory activity towards human leucocyte elastase has been demonstrated on in vitro and in vivo tests. The compounds exhibited inhibitory activities superior to the reference products such as chloromethyl ketone or dichloroisocoumarin.

The substituents of the compounds of formula (I) enabled antioxidant-type properties to be added to the human leucocyte elastase inhibitory activity.

Another subject of the present invention is the pharmaceutical compositions containing as active principle at least one compound of general formula (I) or one of the addition salts thereof with a pharmacologically acceptable base, alone or in combination with one or more inert and non-toxic vehicles or excipients.

Among the pharmaceutical compositions according to the invention, there may more particularly be mentioned those which are suitable for oral, parenteral and nasal administration, plain or coated tablets, sublingual tablets, gelatin capsules, lozenges, suppositories, creams, ointments, dermal gels, aerosols, drinkable and injectable ampoules, etc.

The appropriate dosage varies depending on the age and weight of the patient, the nature and severity of the complaint and the route of administration.

This may be an oral, nasal, rectal or parenteral route. In general, the unit dosage ranges between 10 mg and 300 mg for a treatment taken 1 or 3 times per 24 hours.

A preferred route of administration of the derivatives of the invention is the aerosol route in powder or liquid aerosol form.

The examples which follow illustrate the invention and do not limit it in any way.

The starting materials used are known products or products prepared according to known procedures.

The abbreviations used in the examples are as follows:

| Boc | in place of tert-butoxycarbonyl, |
|---|---|
| Val | in place of valyl, |
| Phi | in place of perhydroindole-2-carbonyl, |
| Bz | in place of benzyl, |
| Valinol-CF$_3$ | in place of: |

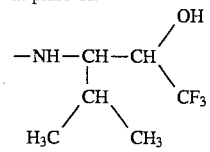

Preparation A:4-[4-Chloro-3-(4-hydroxy-3,5-di-tert-butylphenylthioacetylaminosulfonyl)benzoylatninosulfonyl]benzoic acid Stage A: 4-Hydroxy-3,5-di-tert-butylphenylthioacetic acid 144 mmol of 4-hydroxy-3,5-di-tert-butylthiophenol, 128 mmol of potassium carbonate and 1.44 mmol of tert-butyl bromoacetate are stirred for 7 hours at 70° C. in 280 ml of acetonitrile, under a nitrogen atmosphere, and then for 12 hours at room temperature. After evaporation of the solvent, the residue is taken up in water and extracted with ethyl ether. The organic phase is washed with saturated sodium chloride solution, dried and evaporated. The residue is purified by chromatography on a column of silica, using a chloromethane/cyclohexane mixture (40/60) as eluent. The oil collected is diluted in 150 ml of methylene chloride and 30 ml of trifluoroacetic acid are added to this mixture. After 18 hours at room temperature, the solvent is evaporated off and the expected product is obtained after precipitation in pentane.

Melting point: 130° C.

Stage B: Ethyl 4-chloro-3-(4-hydroxy-3,5-di-tert-butylphenylthioacetylaminosulfonyl)benzoate To 89 mmol of the product obtained in the above stage and 89 mmol of 2-chloro-5-ethoxycarbonylbenzenesulfonamide in 500 ml of tetrahydrofuran are added 17.9 mmol of 2-dimethylaminopyridine and 93 mmol of 1-(3-dimethylaminopropyl)-3-ethylcarbodiimide hydrochloride. The mixture is stirred for 20 hours at room temperature. After evaporation of the solvent, the residue is taken up in ethyl acetate. The organic phase is washed with 10% citric acid solution and then with saturated sodium chloride solution. After drying and evaporation, the expected product is obtained by crystallization from isopropyl ether.

Melting point: 144° C.

Stage C: 4-Chloro-3-(4-hydroxy-3,5-di-tert-butylphenylthioacetylaminosulfonyl)benzoic acid To 7.8 mmol of the compound obtained in the above stage dissolved in 300 ml of ethanol are added, under a nitrogen atmosphere, 155 mmol of 1N sodium hydroxide and 200 ml of water. After stirring for 48 hours at room temperature, the ethanol is evaporated off. The residual aqueous phase is washed with ethyl acetate and then acidified with hydrochloric acid. The oil which separates out is extracted with ethyl acetate. After washing of the organic phase with saturated sodium chloride solution, drying and evaporation, the residue is taken up in pentane and gives the expected product, which crystallizes.

Melting point: 217° C.

Stage D: Ethyl 4-[4-chloro-3-(4-hydroxy-3,5-di-tert-butylphenylthioacetylaminosulfonyl)benzoylaminosulfonyl]benzoate The expected product is obtained by reaction of 58 mmol of the compound described in the above stage with 58 mmol of 4-ethoxycarbonylbenzenesulfonamide according to the process described in Stage B. The expected product is purified by chromatography on a column of silica, using a dichloromethane/methanol/28% aqueous ammonia mixture (90/10/0.5) as eluent.

Melting point: >260° C.

Stage E: 4-[4-Chloro-3-(4-hydroxy-3,5-di-tert-butylphenylthioacetylaminosulfonyl)benzoylaminosulfonyl]benzoic acid 37 mmol of the ester obtained in the above stage are saponified with 112 ml of 1N sodium hydroxide in 250 ml of ethanol and 150 ml of water according to the technique described in Stage C.

EXAMPLE 1

4-[4-Chloro-3-(4-hydroxy-3,5-di-tert-butylphenyl-thio-acetylatninosulfonyl)benzoylarninosulfonyl]benzoyl-(S)Val-(2S,3aS,7aS)Phi-(R,S) Val-CF$_3$ Stage A: Boc-(S)Val-(2S,3aS,7aS)Phi-OBz Using the peptide coupling technique described by W. KONIG and R. GEIGER (Chem. Ber., 103, 788, 1970), 400mmol of Boc-(S)Val-OH and 400 mmol of (2S,3aS, 7aS)Phi-OBz tosylate are reacted together in 700 ml of dimethylformamide (DMF). After filtration of the dicyclohexylurea formed and evaporation of the DMF, the residue is dissolved in ethyl acetate. The organic phase is washed with sodium hydrogen carbonate, 10% citric acid and with saturated sodium chloride solution. After evaporation of the solvent, the residue is taken up in isopropyl ether. The solution is filtered and treated with 5 g of Black 50S for 1 hour at room temperature. The expected product is then obtained after filtration.

Stage B: Boc-(S)Val-(2S,3aS,7aS)Phi-OH

The compound obtained in the above stage is dissolved in 500 ml of ethanol and is hydrogenated for 20 hours, at ambient temperature and pressure, in the presence of 5 g of 5% palladium-on-charcoal. After filtration and evaporation, the residue is taken up in penlane and filtered, and gives the expected product.

Stage C: Boc-(S)Val-(2S,3aS,7aS)Phi-(R,S) Valinol-CF$_3$ 20 mmol of the compound obtained in the above stage and 20 mmol of 1,1,1-trifluoro-3-amino-4-methyl-2-pentanol hydrochloride are coupled according to the peptide coupling technique described in Stage A. The final residue obtained after washing of the ethyl acetate phase and evaporation is taken up in ether. A first mixture of diastereoisomers is filtered. The ether is evaporated off and the second mixture of diastereoisomers is obtained after purification of the residue by chromatography on a column of silica, using a dichloromethane/ethyl acetate mixture (90/10) as eluent. These diastereoisomer mixtures are used without further purification in the following stage.

Stage D: Boc-(S)Val-(2S,3aS,7aS)Phi-(R,S)Val-CF$_3$ 172 mmol of oxalyl chloride are placed in 50 ml of dichloromethane, under a nitrogen atmosphere. The mixture is cooled at −55° C., and 35 ml of dimethyl sulfoxide in 100 ml of dichloromethane are added at this temperature. After stirring for 5 minutes and maintaining the temperature, 73 mmol of the compound obtained in the above stage in 300 ml of dichloromethane are added slowly. The temperature is then brought to −15° C. and the mixture is kept stirring for 10 min. After cooling again to between −55° and −60° C., 75 ml of triethylamine in 100 ml of dichloromethane are added. After returning to room temperature and addition of 300 ml of water, the organic phase is separated off after settling of the phases has taken place and is then washed with 10% citric acid solution until the pH is acidic, and then with sodium chloride solution. After drying and evaporation, the residue is purified by chromatography on a column of silica, using a dichloromethane/ethanol mixture (97.5/2.5) as eluent, and gives the expected product.

Stage E: (S)-Val-(2S,3aS,7aS)Phi-(R,S)Val-CF$_3$ hydrochloride

The product obtained in the above stage is dissolved in 350 ml of dioxane and a stream of hydrogen chloride gas is maintained in this solution for 30 minutes at room temperature. Stirring is continued for 15 hours. The solvent is evaporated off and the expected product is obtained, which is dried.

Stage F: 4-[4-Chloro-3-(4-hydroxy-3,5-di-tert-butylphenylthioacetylaminosulfonyl)benzoylaminosulfonyl]benzoyl-(S)Val-(2S,3aS,7aS)Phi-(R,S)Val-CF$_3$ The expected product is obtained according to the process described in Tet. Lett., 1219, 1975 starting with the compound obtained in the above stage and 30 mmol of the acid described in Preparation A, which are stirred in 350 ml of DMF. After stirring for 20 hours at room temperature, the solvent is evaporated off and the residue is taken up in ethyl acetate and 10% citric acid solution. The organic phase is separated off after settling of the phases has taken place, washed with water until neutral and evaporated. The residue is purified by chromatography on a column of silica, using a dichloromethane/methanol/28% aqueous ammonia mixture (85/15/0.5) as eluent. The expected product is thus obtained and is washed with 10% citric acid solution and then with water until neutral. After drying and evaporation, it is taken up in pentane and filtered.

Elemental microanalysis:

|  | C % | H % | N % | S % | Cl % |
| --- | --- | --- | --- | --- | --- |
| Calculated | 54.66 | 5.78 | 6.37 | 8.75 | 3.23 |
| Found | 54.82 | 5.93 | 6.69 | 8.69 | 3.48 |

EXAMPLE 2

4-[4-Chloro-3-(4-hydroxy-3,5-di-tert-butylphenylthioacetylaminosulfonyl)benzoylaminosulfonyl]benzoyl-(S)Val-(2S,3aS,7aS)Phi-Val-CF$_3$, α-isomer

EXAMPLE 3

4-[4-Chloro-3-(4-hydroxy-3,5-di-tert-butylphenylthio-acetylaminosulfonyl)benzoylaminosulfonyl]benzoyl-(S)Val-(2S,3aS,7aS)Phi-Val-CF$_3$, β-isomer The α and β isomers of the compound of Example 1 in sodium salt form are separated by liquid chromatography on a C18 silica column, using an acetonitrile/sodium hydrogen carbonate (0.05M) mixture as eluent in a gradient ranging from 30% to 100% of acetonitrile.

EXAMPLE 4

[4-Chloro-3-(4-hydroxy-3,5-diterbutylphenyl-thioacetylaminosulfonyl)benzoyl]-(S)Val-(2S,3aS,7aS)Phi-(R,S)Val-CF$_3$ The expected product is obtained according to the process described in example 1 by replacing at stage F, the acid described in the preparation A by the acid described at stage C of the preparation A. The product is purified by chromatography on a column of silica, using a dichloromethane/methanol/ammoniac mixture (90/10/10).

Elemental microanalysis:

|  | C % | H % | N % | S % | Cl % |
| --- | --- | --- | --- | --- | --- |
| calculated | 56,41 | 6,39 | 6,12 | 7,00 | 3,87 |
| found | 56,58 | 6,81 | 6,07 | 6,80 | 3,96 |

PHARMACOLOGICAL STUDY OF THE DERIVATIVES OF THE INVENTION

EXAMPLE 5

Inhibitory Activity Towards Human Leucocyte Elastase in Vitro

The power of the compounds of the invention is determined by the level of inhibition of the action of human leucocyte elastase on a low-molecular-weight peptide substrate according to the technique described by B. M. ASHE et al. (J. Biol. Chem., 256, 11603–11606, 1981). This activity is measured by following the kinetics for hydrolysis of the substrate, resulting in the release of para-nitroaniline which absorbs at a wavelength of 410 nm.

Reactant:
Enzyme: Elastase from human leucocyte sputum (Elastin Products Co.) solubilized to 1000 IU/ml of distilled water, and frozen in 50 ml aliquots at −20° C.
Substrate: methoxysuccinyl-L-alanyl-L-alanyl-prolyl-valine-paranitroanilide
(Sigma Chemical Co.).
Buffer: 0.1M Tris; 0.5M NaCl; pH=7.8.
Equipment:
Spectrophotometer thermostatically regulated to 37° C. equipped with a cell changer.
1 ml polystyrene cell.
Dry water bath set at 37° C.
Procedure:
  The following are introduced into a cell:
  970 µl of buffer
  10 µl of test product or of solvent (concentrated×100)
  10 µl of leucocyte elastase from human sputum at 1/10 dilution
  Shaking and incubation for 15 min at 37° C.

The reaction is started by addition of 10 ml of substrate.
The cell is introduced into the spectrophotometer and the optical density is recorded as a function of time at 410 nm and at 37° C. The initial rate is measured for each concentration of product (or solvent control) studied. Percentages of inhibition relative to the solvent control are calculated:

Percentage of inhibition=100×[(control rate−rate of test product)/control rate]. The 50% inhibitory concentrations ($IC_{50}$) are calculated from the percentages of inhibition by simple linear regression. The results obtained in this test are for the compound of Example 1 $IC_{50}$=26 nM, for the compound of Example 4: 46 nM.

EXAMPLE 6

Inhibitory Activity in Vivo: Model of Acute Hemorrhagic Edema in Hamsters

Tracheal instillation in hamsters of a purified preparation of leucocyte elastase from human sputum results in an acute hemorrhage which may be quantified by measuring the concentration of hemoglobin in the broncho-alveolar washing 18 hours after the instillation of elastase.

The study is carried out on male hamsters weighing 120 to 140 g (Syrian Golden, n=10 per batch). The animals are anesthetized intraperitoneally with pentobarbital at a dose of 40 mg/kg.

The hamsters are anesthetized and the trachea is surgically exposed. The test products are administered using a needle directly into the trachea, in a volume of 0.1 ml at a dose of 15 nM. Leucocyte elastase from human sputum is administered intratracheally 18 hours after administration of the product, at a dose of 50 units per animal, in a volume of 0.2 ml.

The animals are sacrificed using a lethal dose of pentobarbital, 3 hours after the instillation of elastase, and a broncho-alveolar washing with physiological saline is carried out. The degree of hemorrhaging is quantified by a colorimetric method, which enables the hemoglobin concentration to be assayed (Boeringer hemoglobin combination test). The results are expressed as a percentage inhibition of the hemorrhaging. The compound of the present invention is an effective inhibitor of human leucocyte elastase which prevents or decreases the hemorrhaging induced by intratracheal instillation of human leucocyte elastase. The results obtained in this test for the compound of Example 1 demonstrate a noteworthy duration of action with an inhibition of 53% at time 18 h after intratracheal administration and for the compound of Example 4, an inhibition of 23% in the same conditions.

EXAMPLE 7

Lipid Peroxidation Study

A/ The study was performed on rat liver microsomes in the presence of $Fe^{3+}$(100 mM) and ascorbate (100 mM). The malondialdehyde (MDA) is assayed by means of the thiobarbituric acid method (spectrophotometry l=532 nm) according to the technique described by N. PAYA et al. (Biochem. Pharmacol., vol. 44, No. 2, p. 205–214, 1992). The product of Example 1 possesses a 50% inhibitory activity ($IC_{50}$) of $10^{-6}$M on lipid peroxidation in the system studied.

B/ The action of the derivatives of the present invention was studied on the oxidative modification of LDLs induced by copper sulfate.

Human LDLs are incubated for 24 hours in the presence of $10^{-5}$M copper sulfate and in the absence or presence of the compounds tested ($10^{-9}$M to $10^{-4}$M). After incubation, the LDL peroxidation is evaluated by electrophoresis on agar gel and by the formation of malondialdehyde (MDA) (Patharsrathy S et al., J. Clin. Invest. 77, 641–644, 1986).

The activity of the products is evaluated by calculating the concentrations which reduce by 50% ($IC_{50}$) the production of MDA relative to the control experiments. The compounds of Examples 1 and 4 of the present invention exhibit an $IC_{50}$ of $3\times10^{-7}$M on human LDL peroxidation induced by copper sulfate.

EXAMPLE 8

Pharmaceutical Composition
Preparation formula for 1000 tablets containing 10 mg doses

| | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

We claim:
1. A compound of formula (I):
in which:

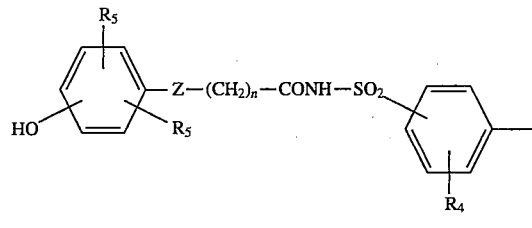

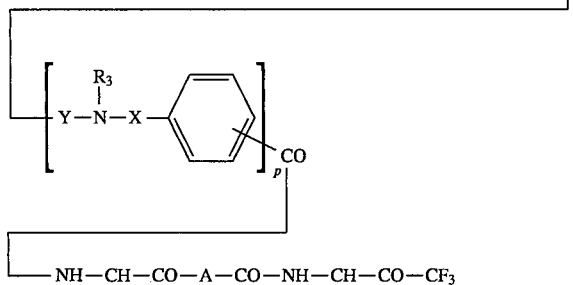

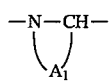

$R_1$ represents linear or branched ($C_1$–$C_6$) alkyl or ($C_3$–$C_7$) cycloalkyl,
$R_2$ represents linear or branched ($C_1$–$C_6$) alkyl or ($C_3$–$C_7$) cycloalkyl,
$R_3$ represents hydrogen or linear or branched ($C_1$–$C_6$) alkyl,
$R_4$ represents halogen or linear or branched ($C_1$–$C_6$) alkyl or linear or branched ($C_1$–$C_6$) alkoxy,
$R_5$ represents linear or branched ($C_1$–$C_6$) alkyl,
X and Y, which are different, represent CO or $SO_2$,
n represents 1, 2 or 3,
p represents 1,
Z represents sulfur or oxygen,
A represents any one of the following groups:

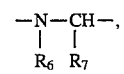

in which:
$A_1$ represents, with the nitrogen and carbon atoms to which it is attached, a 2-azabicyclo[2.2.2]octane, 2-azabicyclo[2.2.1]heptane, perhydroindole, perhydroisoindole, indoline, isoindoline, perhydroquinoline, perhydroisoquinoline, 1,2,3,4-tetrahydroisoquinoline, 1,2,3,4-tetrahydroquinoline, cyclopenta[b]pyrrolidine, 1,3-thiazolidine or pyrrolidine ring system, or,

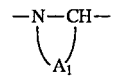

in which:
$R_6$ represents hydrogen, linear or branched ($C_1$–$C_6$) alkyl, ($C_3$–$C_6$) cycloalkyl or 2-indanyl,
$R_7$ represents hydrogen or linear or branched ($C_1$–$C_6$) alkyl,
which compounds of formula (I) comprise the corresponding hydrates of the ketone function $COCF_3$,
the enantiomers, diastereoisomers and epimers thereof and the addition salts thereof with a pharmaceutically acceptable base.

2. A compound of claim 1, wherein A represents the group $$-N-CH- \atop A_1$$

as defined in claim 1.

3. A compound of claim 1, wherein A represents a perhydroindole ring.
4. A compound of claim 1, wherein n is equal to 1.
5. A compound of claim 1, wherein Z represents a sulfur atom.
6. A compound of claim 1, which is 4-[4-chloro-3-(4-hydroxy-3,5-di-tert-butylphenylthioacetylaminosulfonyl)benzoylaminosulfonyl]benzoyl-(S)Val-(2S,3aS,7aS)Phi-(R,S)Val-$CF_3$.
7. The compound claim 1, which is [4-chloro-3-(4-hydroxy-3,5-diterbutylphenylthioacetylaminosulfonyl)benzoyl]-(S)Val-(2S,3aS,7aS)Phi-(R,S)Val-$CF_3$.
8. A method for treating a mammal afflicted with a disease requiring a human leucocyte elastase inhibitor comprising the step of administering to the mammal an amount of a compound of claim 1 which is effective for alleviation of said condition.
9. A pharmaceutical composition useful as human leucocyte elastase inhibitor comprising as active principle an effective amount of a compound claim 1, together with one or more pharmaceutically acceptable excipients or vehicles.

* * * * *

UNITED STATES PATENT AND TRADEMARK OFFICE
CERTIFICATE OF CORRECTION

PATENT NO. : 5,567,804  Page 1 of 2
DATED : October 22, 1996
INVENTOR(S) : Guillaume de Nanteuil, Bernard Portevin, Emmanuel Canet It is certified that error appears in the above-indentified patent and that said Letters Patent is hereby corrected as shown below:

Title Page, [57] ABSTRACT, Column 2, 4 lines below last formula: Delete "thereof" and insert -- the --.

Column 2, line 37: "X and Y.........." should start a separate line.

Column 2, line 66: "R7" should read -- $R_7$ --.

Column 3, line 22: "(IID)," should read -- (III), --.

Column 5, line 66: "benzoylanino" should read -- benzoylamino --.

Column 6, line 20: "nylthioacetylarnino" should read -- nylthioacetylamino --.

Column 6, line 36: "ioacetylarnino" should read -- ioacetylamino --.

Column 7, line 4: "acetylatnino" should read -- acetylamino -- and "benzoylarnino" should read -- benzoylamino --.

Column 7, line 25: "penlane" should read -- pentane --.

Column 11, line 3: Delete "in which,". Preliminary Claim 1, line 2:.

UNITED STATES PATENT AND TRADEMARK OFFICE
CERTIFICATE OF CORRECTION

PATENT NO. : 5,567,804
DATED : October 22, 1996
INVENTOR(S) : Guillaume de Nanteuil, Bernard Portevin, Emmanuel Canet It is certified that error appears in the above-indentified patent and that said Letters Patent is hereby corrected as shown below:

Column 11, line 24: Insert -- in which: -- after formula.

Column 12, line 34: Delete "claim 1, which is". <u>Claim 7, line 1:</u>.

Column 12, line 38: "disease" should read -- condition --. <u>Claim 8, line 1:</u>.

Column 12, line 45: Insert -- of -- after "compound". <u>Claim 9, line 2:</u>.

Column 12, line 46: Insert a -- - -- (dash) between "pharmaceutically" and "acceptable", <u>Claim 9, line 3:</u>.

Signed and Sealed this

Seventh Day of January, 1997

Attest:

BRUCE LEHMAN

*Attesting Officer*     *Commissioner of Patents and Trademarks*